United States Patent [19]

Stroz et al.

[11] 4,419,346

[45] Dec. 6, 1983

[54] **METHOD AND COMPOSITION TO INHIBIT THE GROWTH OF *STREPTOCOCCUS MUTANS* BY THE USE OF SACCHARIN/FLUORIDE COMBINATION**

[75] Inventors: John J. Stroz, Monroe, Conn.; Andrew M. Slee, Averill Park, N.Y.

[73] Assignee: Nabisco Brands, Inc., Parsippany, N.J.

[21] Appl. No.: 407,987

[22] Filed: Aug. 13, 1982

[51] Int. Cl.³ .................. A61K 7/18; A61K 9/68; A61K 33/16

[52] U.S. Cl. .................. 424/151; 424/48; 424/52; 424/54; 424/49; 424/270; 426/3; 426/548

[58] Field of Search .................. 424/48, 52, 151, 270; 426/3–6, 548

[56] References Cited

U.S. PATENT DOCUMENTS

| | | |
|---|---|---|
| 2,627,493 | 2/1953 | Merckel et al. ............ 424/52 |
| 2,913,373 | 11/1959 | Weisz et al. ............ 424/52 |
| 3,075,884 | 1/1963 | Bilotti et al. ............ 424/48 |
| 3,119,743 | 1/1964 | Ericsson ............ 424/52 |
| 3,227,618 | 1/1966 | Manahan et al. ............ 424/52 |
| 3,282,792 | 11/1966 | Fiscella ............ 424/52 |
| 3,431,339 | 3/1969 | Gyarmathy et al. ............ 424/52 |
| 3,531,564 | 9/1970 | Bouchal et al. ............ 424/52 |
| 3,590,120 | 6/1971 | Muhler ............ 424/48 |
| 4,078,053 | 3/1978 | De Paola ............ 424/52 |
| 4,118,471 | 10/1978 | Pensak ............ 424/52 |
| 4,265,877 | 5/1981 | Tenta ............ 424/52 |
| 4,291,045 | 9/1981 | Mackay et al. ............ 424/48 |

FOREIGN PATENT DOCUMENTS 2420970  11/1979  France ............ 424/48

OTHER PUBLICATIONS

Linke et al., Z. Naturforsch. C. Biosci., (1976), 31c, (5/6): 245–251, Physiological Effects of Sucrose Substitutes and Artificial Sweeteners on Growth Pattern and Acid Production of Glucose-Grown Streprococcus Mutans Strains in Vitro.

Linke, Z. Naturforsch. C. Biosci., (1977), 32c, (9/10): 839–843, Growth Inhibition of Glucose-Grown Cariogenic and Other Streptococci by Saccharin in Vitro.

Slee et al., FNDH Conference, (1981), (14 pages), The Effect of Sodium Saccharin on the Growth of Cariogenic and Other Selected Plaque-Forming Streptococci.

*Primary Examiner*—Shep K. Rose
*Attorney, Agent, or Firm*—Richard Kornutik

[57] ABSTRACT

A method and composition for treating teeth to reduce dental caries is provided wherein the teeth are contacted with a synergistic combination of a saccharin material, and a fluoride material, for example, as contained in a chewing gum composition, the combination of saccharin material and fluoride material being present in an amount sufficient to inhibit growth of *Streptococcus mutans* in the presence of a fermentable carbohydrates in the oral cavity.

5 Claims, 14 Drawing Figures

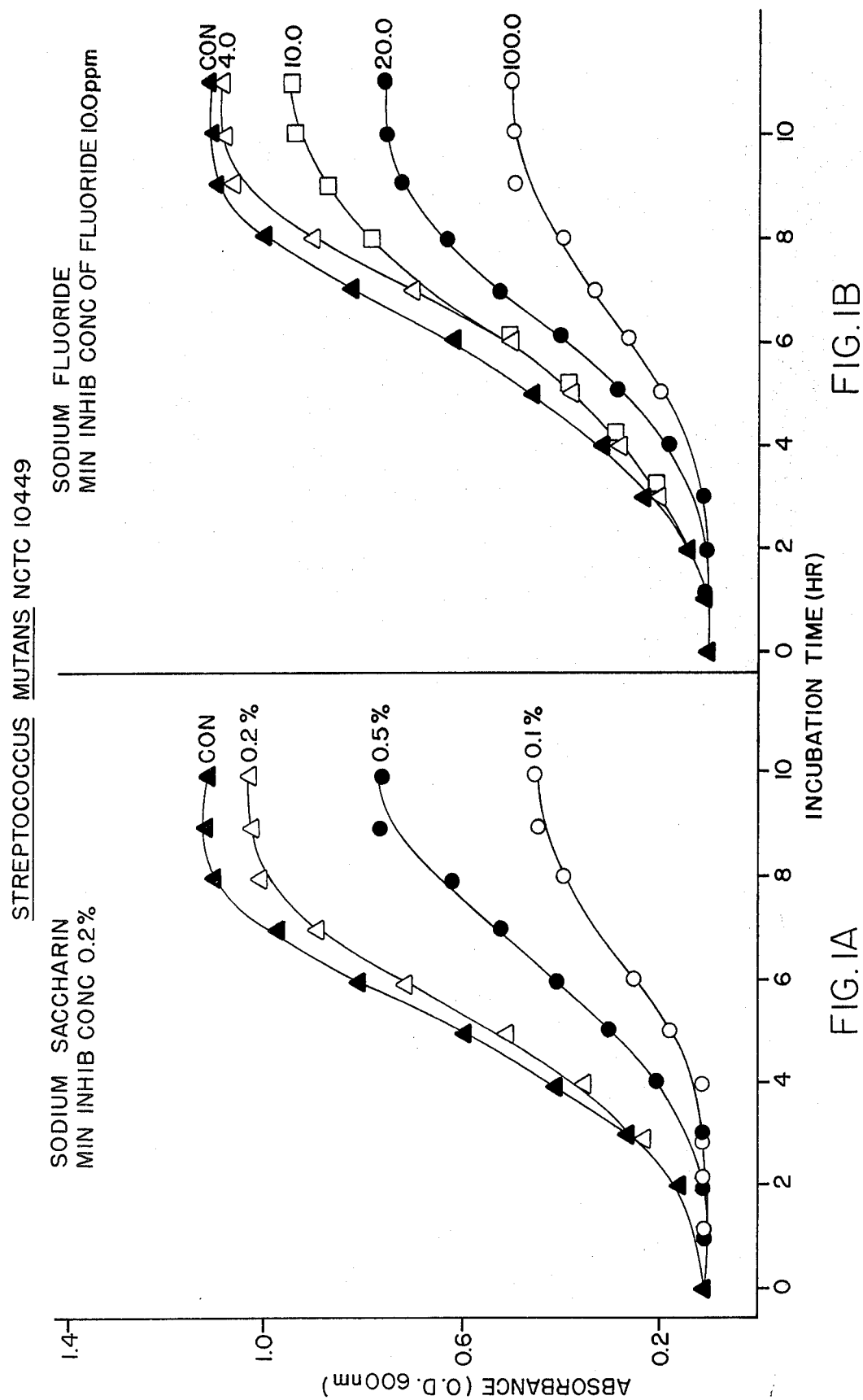

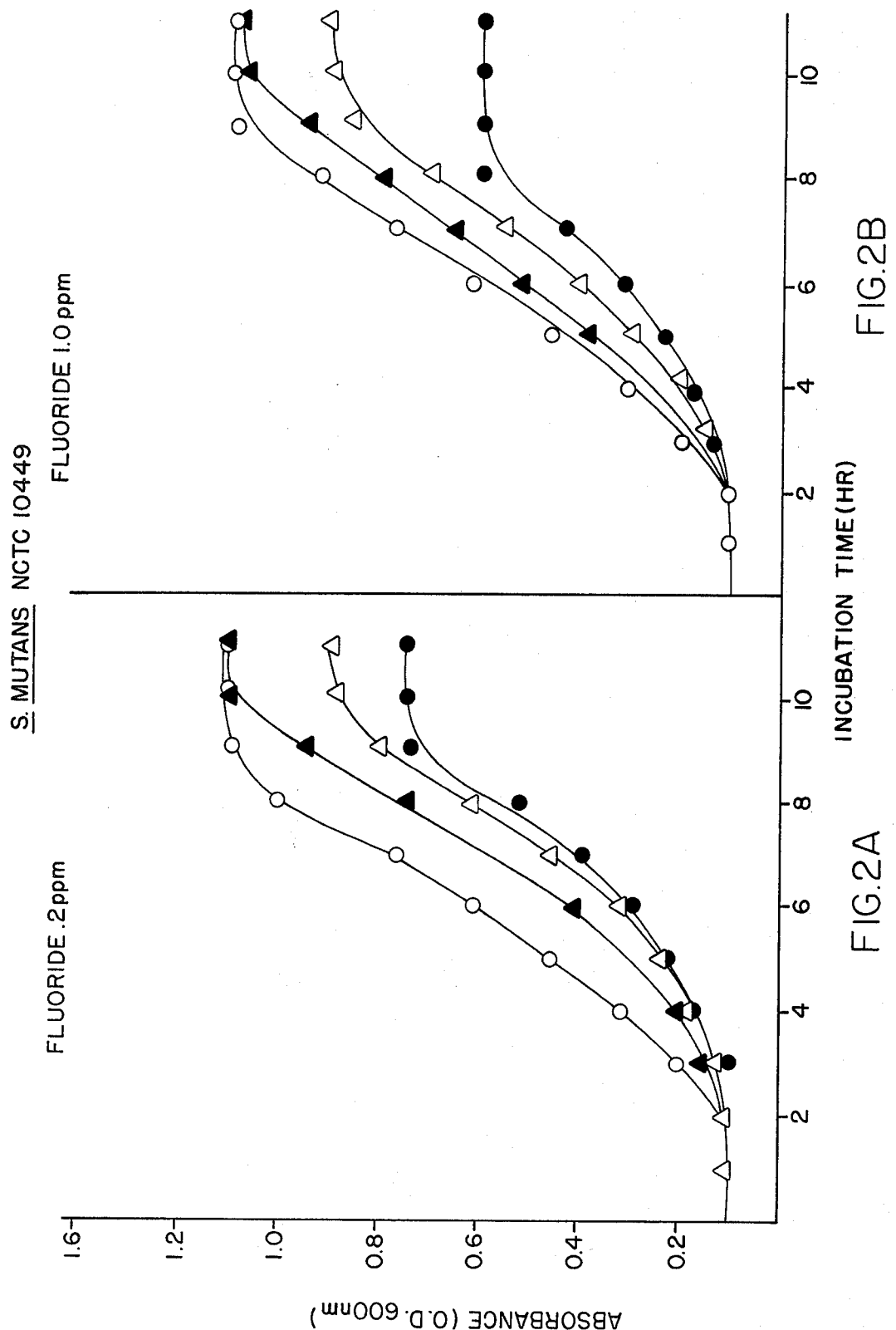

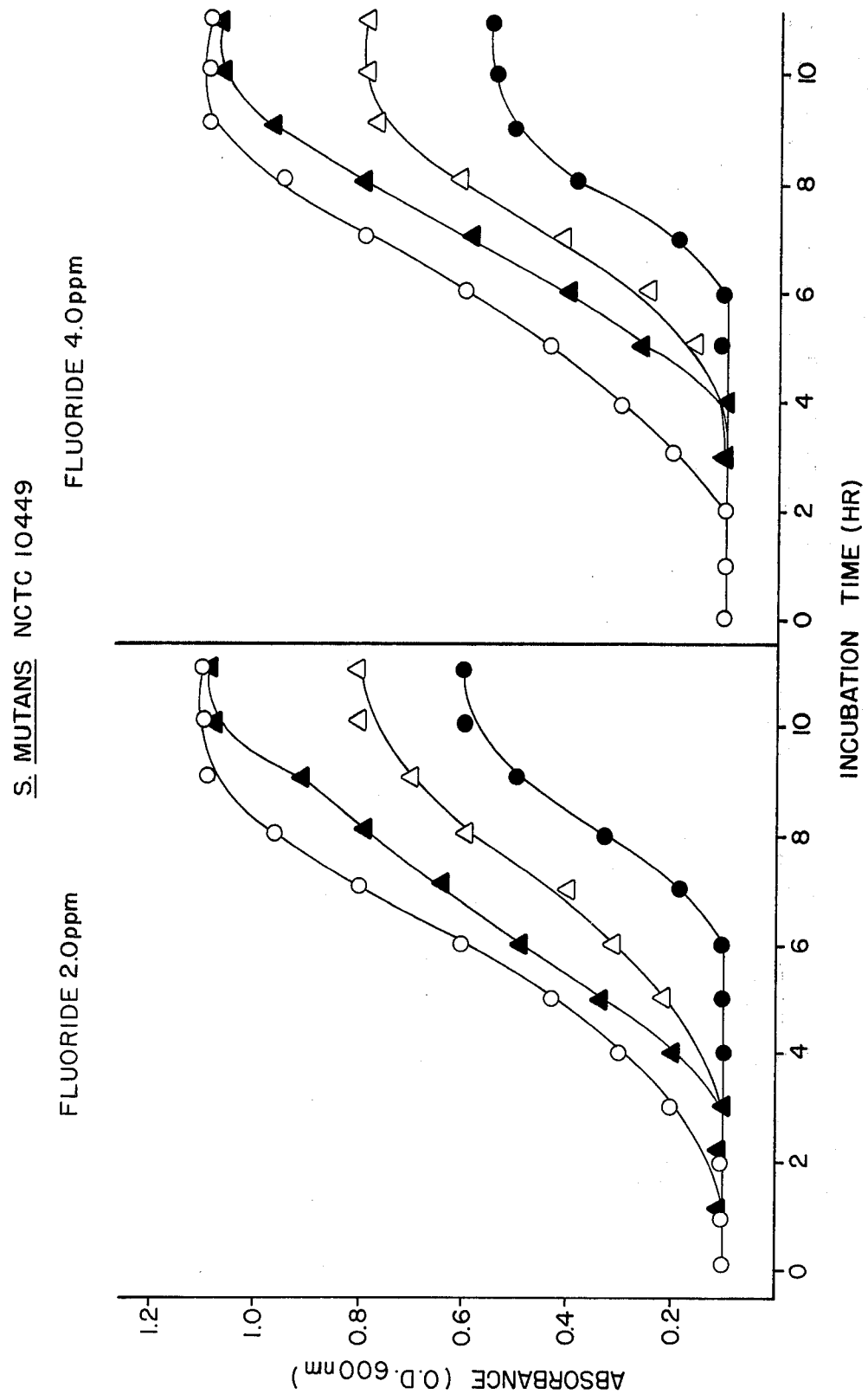

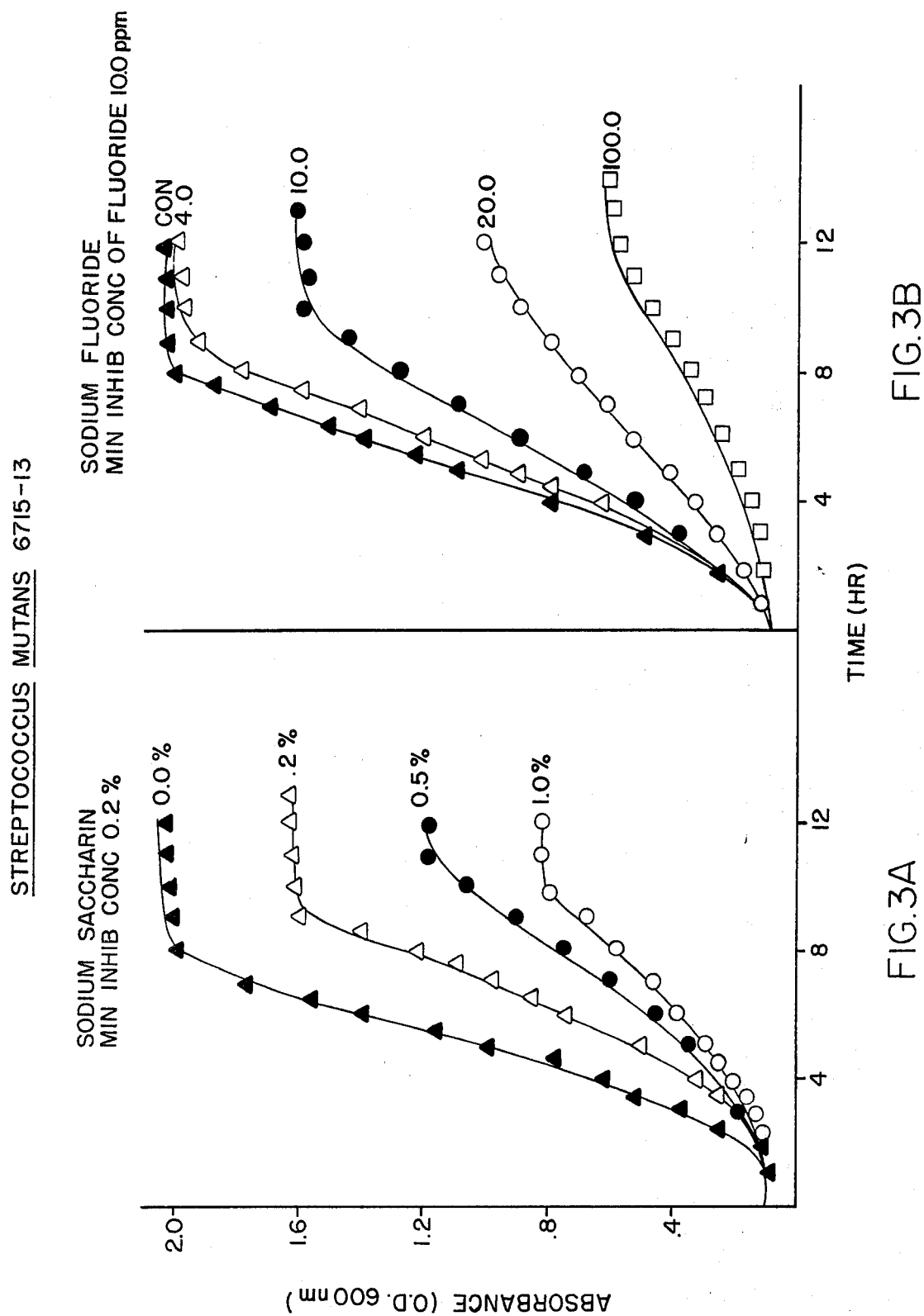

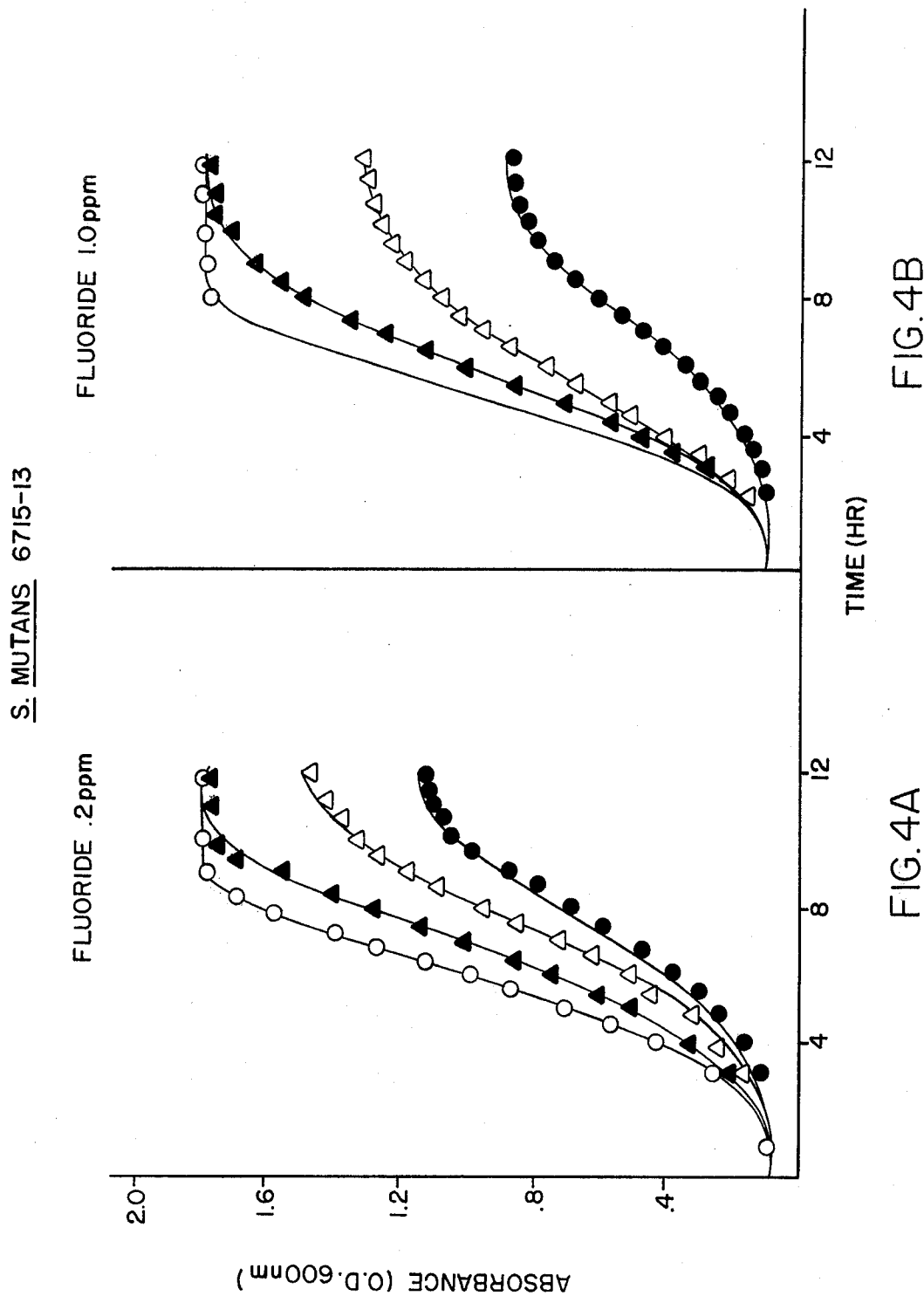

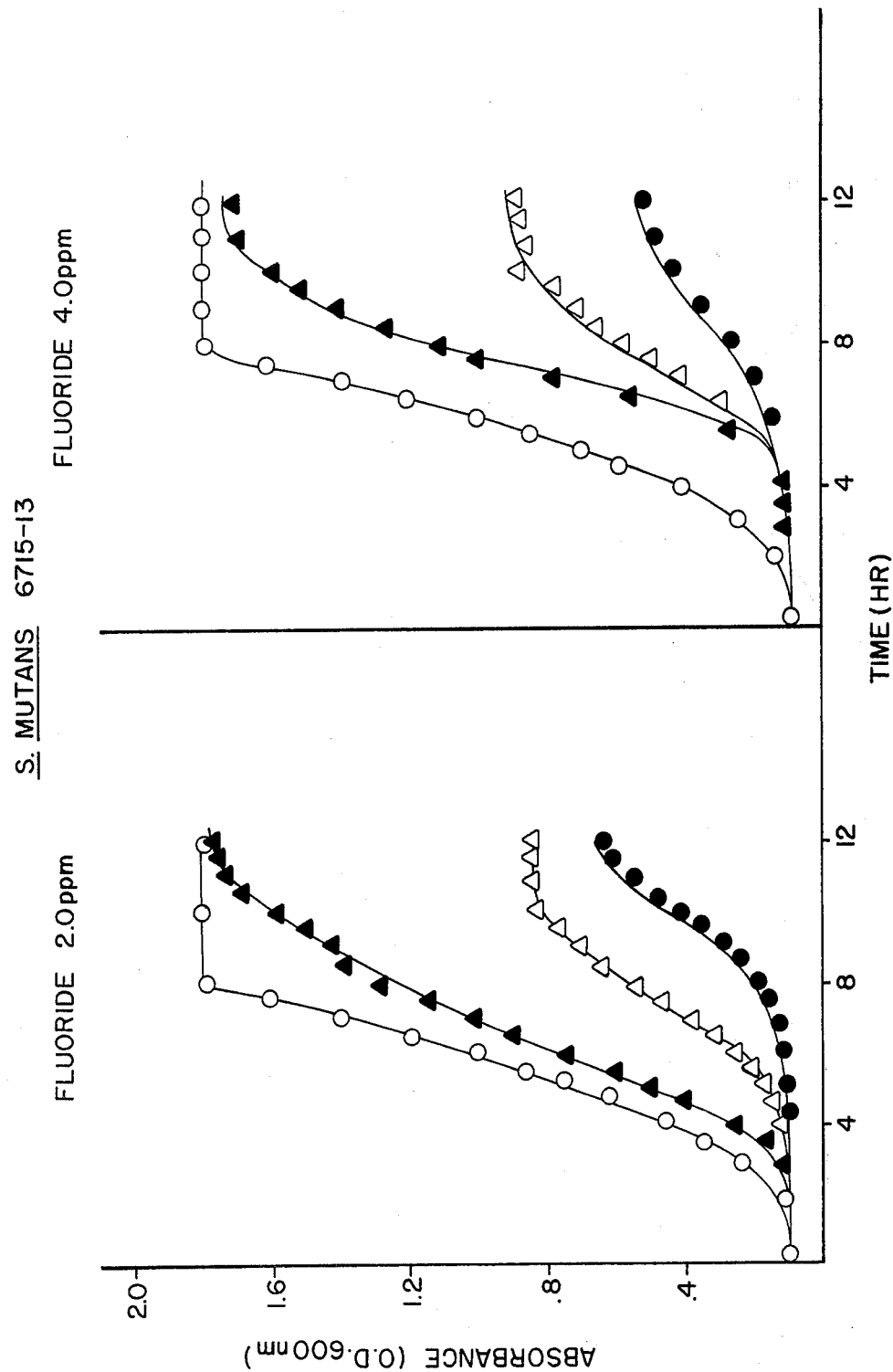

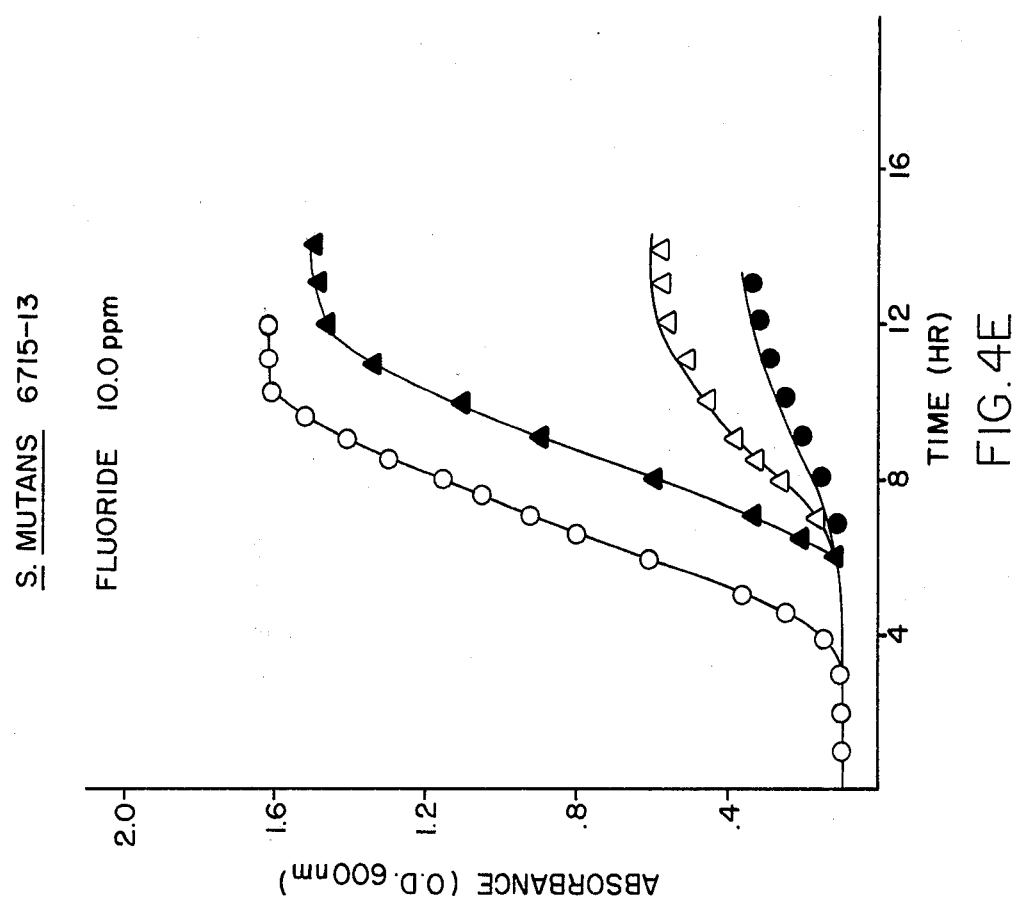

METHOD AND COMPOSITION TO INHIBIT THE GROWTH OF *STREPTOCOCCUS MUTANS* BY THE USE OF SACCHARIN/FLUORIDE COMBINATION

BACKGROUND OF THE INVENTION

The present invention relates to a method and a composition for preventing or reducing dental caries by inhibiting the growth of *Streptococcus mutans* in the oral cavity.

Foods containing fermentable carbohydrates such as mono-, di-, and polysaccharides, have long been recognized as a major contributing cause of dental caries. These carbohydrates have, in particular, been associated with the initiation of dental caries especially since they are an easily utilizable source of nutrition for bacteria, such as *Streptococcus mutans* found in the oral cavity, which bacteria is primarily responsible for the formation of plaques on the surface of the teeth.

*S. mutans* is generally recognized as the most cariogenic oral bacteria because of its ability to adhere to and colonize on enamel surfaces through formation of a dextran matrix, especially in the presence of sucrose. In this way the *S. mutans* is firmly affixed adjacent the surface of teeth in which location fermentation of carbohydrates leads to the formation of organic acid and, in particular, lactic acid which can solubilize components of the tooth enamel.

In an effort to reduce incidence of tooth decay, artificial sweeteners, such as saccharin salts and cyclamate salts have been employed as substitutes for natural sweeteners in many foods. The use of non-fermentable carbohydrates such as polyhydric alcohols such as sorbitol, mannitol and xylitol have also been employed either alone or in combination with artificial sweeteners in place of natural sweeteners in chewing gums and confections. However, these non-sugar bulking agents have been found to be inferior in sweetness to the mono- and disaccharides normally used.

It has been found that the use of saccharin material in foods, confections, chewing gum, beverages and the like as a substitute for fermentable carbohydrates or in combination with sugars and/or polyhydric alcohols provides an especially effective means to prevent and inhibit tooth decay. The saccharin material has been found to inhibit growth of strains of *S. mutans*, generally recognized to be the most virulent of the cariogenic bacteria. See U.S. Pat. No. 4,291,045 to Mackay, et al.

Sodium saccharin is inert to metabolism by oral microorganisms and possesses the desired organoleptic property of sweetness, thereby satisfying the criteria for an artificial sweetener. In addition to its value as an artificial sweetener, recent studies have demonstrated that sodium saccharin at concentrations greater than 0.2% (by weight) also possesses inhibitory activities against various oral plaque-forming streptococci (Slee and Tanzer, 5th Ann. ADAHF Conf., 1981). (All percentages herein are by weight unless stated otherwise.)

The inhibitory effect of fluoride in compositions on the metabolism of cariogenic microorganisms in the oral cavity has often been demonstrated. See U.S. Pat. No. 4,265,877 to Tenta, and U.S. Pat. Nos. 2,700,012 and 2,627,493 to Merkel, et al. Although fluorides and saccharin individually are known inhibitors of bacterial growth in the oral cavity, it has been found that the combination of fluoride and saccharin is surprisingly effective in inhibiting the growth of *S. mutans* and other cariogenic bacteria when compared to the inhibitory effect of equal amounts of the individual components.

It is an object of this invention to provide a method and a composition for preventing or reducing dental caries by inhibiting the growth of *S. mutans* in the presence of fermentable carbohydrates in the oral cavity.

It is another object of this invention to provide a method for preventing or reducing dental caries by the normal consumption or use of confections and other food or cosmetic products especially chewing gum.

It is a further object of this invention to provide a method and a composition for preventing or reducing dental caries utilizing a combination of saccharin and fluoride.

The achievement of these and other objects will be apparent from the following description of the subject invention.

SUMMARY OF THE INVENTION

In accordance with the present invention a method is provided for treating teeth to inhibit or prevent dental caries in the presence of fermentable carbohydrates, wherein the teeth are contacted with a synergistic combination of saccharin and fluoride in an amount sufficient to inhibit growth of *S. mutans* present in the oral cavity in general or on the teeth in particular. Further, the present invention also concerns a synergistic combination of saccharin and fluoride which will reduce dental caries when incorporated in confections, chewing gum, and other food product forms.

In particular this invention relates to a method of treating teeth to inhibit or prevent dental caries which comprises solubilizing in saliva, during mastication/ingestion, a composition comprising a synergistic combination of a saccharin and a fluoride in an amount effective to inhibit or prevent the growth of cariogenic microorganisms in the presence of fermentable carbohydrates.

This invention may also be described as being related to a method of inhibiting the growth of *S. mutans* which comprises contacting *S. mutans* with saliva containing a synergistic combination of a saccharin and a fluoride in an amount effective to inhibit the growth of *S. mutans* while in the presence of a fermentable carbohydrate.

This invention is also directed to compositions of matter which may be usefully employed in the method of this invention. These compositions of matter include a chewing gum, other confections, a beverage, desserts, or other food products, each of which contains a synergistic combination of a saccharin and a fluoride in an amount effective to inhibit or prevent caries in the presence of a fermentable carbohydrate when any of said compositions of matter are ingested.

BRIEF DESCRIPTION OF THE DRAWINGS

FIG. 1A is a graph showing the inhibiting effect of sodium saccharin on *S. mutans* NCTC 10449.

FIG. 1B is a graph showing the inhibiting effect of sodium fluoride on *S. mutans* NCTC 10449.

FIGS. 2A through 2E are a series of graphs showing the inhibiting effect of various combinations of sodium saccharin and sodium fluoride on *S. mutans* NCTC 10449.

FIG. 3A is a graph showing the inhibiting effect of sodium saccharin on *S. mutans* 6715-13.

FIG. 3B is a graph showing the inhibiting effect of sodium fluoride on *S. mutans* 6715-13.

FIGS. 4A through 4E are a series of graphs showing the inhibiting effect of various combinations of sodium saccharin and sodium fluoride on *S. mutans* 6715-13.

DESCRIPTION OF THE PREFERRED EMBODIMENTS

Figure 2E:
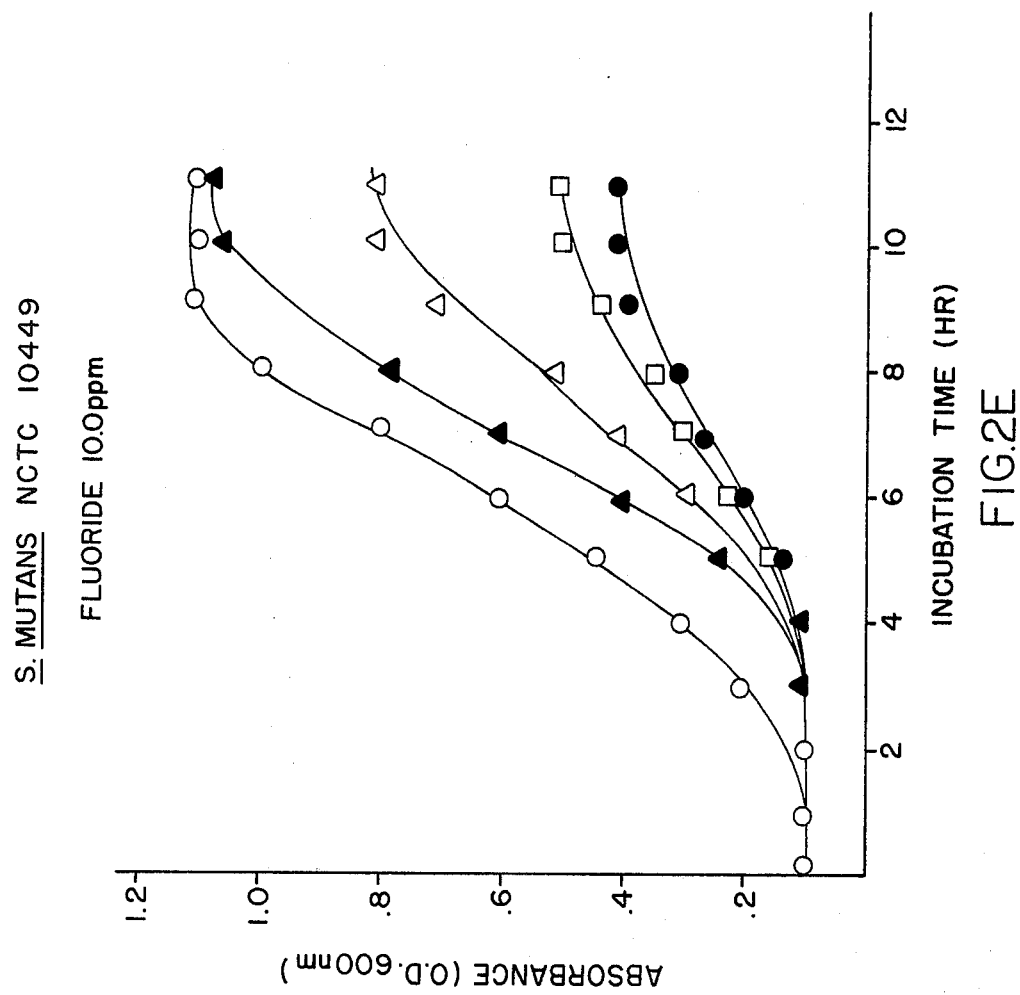

The present invention relates to a method and compositions of matter which effectively inhibit or prevent dental caries. More specifically, it relates to combinations of saccharin and fluoride which act synergistically to inhibit or prevent dental caries by inhibiting the growth of *S. mutans* present in the oral cavity.

The terms "saccharin", "saccharin compound", "saccharin material", "saccharin salt" and similar terms as employed herein include the readily available soluble saccharin salts, such as sodium saccharin, potassium saccharin, calcium saccharin, ammonium saccharin and the like or the relatively insoluble forms of saccharin, such as the free acid form of saccharin.

The terms "fluoride", "fluoride compound", "fluoride material", "fluoride salt" and similar terms as employed herein include the readily available soluble fluoride salts, such as sodium fluoride, potassium fluoride, ammonium fluoride, stannous fluoride and the like or the relatively insoluble forms of fluoride, such as calcium fluoride, strontium fluoride and mono-fluorophosphate.

In carrying out the method of the invention, the combination of a saccharin compound and a fluoride compound will usually be employed in conjunction with a non-toxic edible carrier to form a food, confection, chewing gum, beverage and the like. While the saccharin compound is usually employed in amounts ranging from about 0.1 to about 1% or more by weight of the total composition, by use of the present invention such ranges of saccharin can be effectively reduced.

The essence of the present invention is the synergistic effect of inhibiting the growth of *S. mutans* which is achieved when a saccharin and a fluoride are employed in combination in effective concentrations in the presence of fermentable carbohydrates, especially in the oral cavity. Smaller quantities of each of these materials are required to obtain effective perturbation of growth of *S. mutans* than if each were employed alone. These results are particularly surprising since each compound apparently affects different aspects of the metabolism of *S. mutans*. Sufficient quantities of each material are added to the composition of matter of interest to provide effective amounts of the combination of a saccharin and a fluoride in the oral cavity. Based on previous knowledge of the amounts of each required when used alone, the effective amount must provide in the saliva at least 0.2% saccharin or at least 10 ppm fluoride. However, it has now been found that significantly reduced level of each component when used in combination will achieve the same growth inhibiting effect. Several examples of useful low concentration levels when sodium fluoride and sodium saccharin are employed in combination are set forth below for illustrative purposes.

| Fluoride (ppm) (Present in the form of Sodium Fluoride) | Sodium Saccharin (%) | Effect on *Streptococcus mutans* |
|---|---|---|
| 0.2 | ≧0.1 | Decreased growth yield |
| 1.0 | ≧0.1 | Decreased growth yield |
| 2.0 | ≧0.05 | Increased growth lag |
| 2.0 | ≧0.1 | Decreased growth yield |
| 2.0 | ≧0.2 | Decreased growth yield |
| 10.0 | ≧0.01 | Increased growth lag |
| 10.0 | ≧0.05 | Decreased growth yield |

With these data as a guide and without an undue amount of experimentation, those skilled in the art can select appropriate minimum levels of the synergistic combinations of saccharin and fluoride to incorporate in the carrier of interest to provide the desired degree of *S. mutans* inhibition of the growth.

While the above combinations represent very low levels of concentration of the specific components, the present invention contemplates the use of any concentration level convenient to achieve the desired result for the specific carrier. Thus for example 100 ppm of a fluoride may be used with as much as 1.0% of a saccharin to achieve an inordinately high growth inhibition unexpected when compared to the efficacy of similar concentrations of the individual components.

It appears that the effectiveness of the combination of a saccharin and a fluoride in inhibiting the growth of *S. mutans* increases with increasing concentrations of the saccharin and the fluoride and exposure or contact time. Thus, the presence of relatively small amounts of a saccharin compound and a fluoride compound, solubilized in the saliva over extended periods of time (for example, 1 to 300 mg of saccharin compound and fluoride compound over a period of 5, 10, 20, 30 minutes or more) is, for the purposes of the present invention, more desirable than the presence of peak amounts of a saccharin compound and a fluoride compound solubilized in the saliva for relatively short periods of time (for example, 1 to 300 mg of saccharin compound and fluoride compound over a period of 1 to 4 minutes). Thus, the combination of a saccharin compound and a fluoride compound will preferably be provided in a form or composition so that it may be controlledly or slowly released and solubilized in relatively small quantities in the saliva over extended periods of time; moreover, although large amounts of saccharin compound-fluoride compound combination may be initially present, at any given time, amounts of saccharin material which are organoleptically acceptable (that is, below the bitterness threshold and below the undesirably oversweet threshold) will be solubilized in the saliva and available for tasting.

The sources of saccharin and fluoride ions, especially the soluble saccharin and fluoride salts, will thus preferably be provided in a form to ensure relatively slow release or solubilization in the saliva. Thus, for example, the combination of a saccharin compound and a fluoride compound may be coated with, integrated with, or encapsulated with non-toxic, water-insoluble, polymeric substances such as polyvinyl esters, as disclosed in U.S. Pat. Nos. 3,826,847 and 3,795,744, organic acids as disclosed in U.S. Pat. No. 3,761,288, or other known edible materials as, for example, any of the fusing agents as disclosed in U.S. Pat. No. 3,928,633, as well as hydrophilic colloids such as ethyl cellulose, paraffin wax or sodium alginate. The combination of a saccharin compound and a fluoride compound thus-modified and employed in conjunction with conventional carriers as described above, will be slowly solubilized in the saliva over extended periods of time.

Where the combination of a saccharin compound and a fluoride compound is employed in a chewing gum composition, in order to achieve slow release, the compounds will be employed in particulate form having an average particle size of below about 150 microns (about 100 mesh), and will be incorporated into the gum base portion of the chewing gum. The particulate saccharin compound and the fluoride compound will be substantially retained in the gum base, and during chewing thereby undergo a slow and controlled release into the saliva. An average stick or tablet of gum will preferably contain from about 1.5 to about 25.0 mg of the combination of a saccharin compound and a fluoride compound.

It is well known that fine pulverization of crystals or poorly soluble materials or slowly dissolving materials of even good solubility greatly increases the surface area thereof, which, concommitantly increases the solubility rate. However, it has been surprisingly and unexpectedly found that finely divided saccharin compounds, such as finely powdered free saccharin acid, or the soluble saccharin salts, when incorporated into chewing gum base do just the opposite; the extraction rate of such saccharin compounds from the gum base during chewing is reduced with decreasing particle size. The result is that relatively small concentrations of solubilized saccharin compound (albeit at a concentration above the organoleptic sweetness threshold thereof) will be present in the saliva over a prolonged period. The reason for this effect is that at the finer particle sizes, the saccharin compound is more protected from direct contact with saliva by the gum base. This thereby results in a controlled release of saccharin compound from the gum base. Finely divided fluoride compounds behave in a similar manner.

The slowly or controlledly released saccharin and fluoride containing chewing gum compositions employed in the method of the invention may be prepared by admixing melted gum base with a plasticizer, such as a syrupy substance, for example, corn syrup, or a modified starch syrup or sorbitol syrups, at a temperature ranging from about 180° to about 210° F., to form a base-syrup mix, optionally adding flavor oil to the mix, during the first five minutes of mixing while the mix is folding well admixing the base-syrup mix with a particulate saccharin compound and a fluoride compound to form a continuous gum mass having the particles of saccharin compound intimately dispersed therein, and thereafter, optionally admixing the above mix with one or more easily extractable water-soluble sweeteners, such as natural sugar, soluble saccharin salts, water-soluble food acid and/or flavors. The resulting mix is then formed into sticks or tablets of chewing gum employing conventional techniques.

In carrying out the above method, it is preferred that the saccharin compound and the fluoride compound be poorly water-soluble, such as the free saccharin acid and calcium fluoride, strontium fluoride, and the like, so that they will not dissolve in the plasticizer (which normally will be an aqueous plasticizer such as corn syrup) before it is transferred to the gum base. However, where nonaqueous plasticizers are employed, the saccharin material and the fluoride material may be of the water-soluble type, such as the sodium saccharin and sodium fluoride salts.

Where it is desired to employ soluble saccharin and fluoride salts in a chewing gum containing an aqueous plasticizer, the soluble saccharin and fluoride salts will be added to the gum base ingredients before the aqueous plasticizer is added thereto. In this manner, the soluble saccharin and fluoride salts will be transferred to the gum base and will not be first dissolved in the plasticizer.

In addition, particles of water-soluble saccharin and/or fluoride salt may be treated to make them less soluble or even insoluble such as by conventional coating or encapsulating techniques as described above, for example, as described in U.S. Pat. Nos. 3,795,744 and 3,826,847. The so-treated particles may be added to the gum base either before or after plasticizer (aqueous or non-aqueous) is added thereto. Regardless of the solubility of the saccharin compound and the fluoride compound, it is preferred that the particles of these compounds have an average particle size of less than 150 microns to ensure slow controlled release into the saliva.

By following the above procedures, the finely divided saccharin and fluoride compounds will be incorporated and retained in the gum base and will undergo controlled release in the mouth for periods of up to 30 minutes or more to provide concentrations of the saccharin and fluoride compounds below the bitter threshold thereof, but in sufficient amounts to inhibit the growth of *S. mutans* and to provide pleasant sweet taste.

The chewing gum will include a relatively water-insoluble, water-impenetrable gum base in an amount ranging from about 8 to about 50%, and preferably from about 15 to 30% by weight of the chewing gum composition.

In general, the gum base is prepared by heating and blending various ingredients, such as, natural gums, synthetic resins, waxes, plasticizers, etc., in a manner well known in the art. Typical examples of the ingredients found in a chewing gum base are masticatory substances of vegetable origin, such as chicle, crown gum, nispero, rosidinha, jelutong, pendare, perillo, niger gutta, tunu, etc., masticatory substances of synthetic origin, such as butadiene-styrene polymer, isobutylene-isoprene copolymer, petroleum wax, polyethylene, polyisobutylene, polyvinylacetate, etc., plasticizers, such as lanolin, stearic acid, sodium stearate, potassium stearate, etc., antioxidants, such as, butylated hydroxyanisole, butylated hydroxytoluene, and propyl gallate.

The water-insoluble gum base may consist of any of the various bases disclosed for example in U.S. Pat. Nos. 3,052,552 and 2,197,719. Typical ingredients included in gum base compositions are the following:

|  | Parts by Weight |
| --- | --- |
| Base I |  |
| Ester gum | 88 |
| Rubber latex solids | 10 |
| Lecithin | 2 |
| Base II |  |
| Chicle | 30 |
| Jelutong | 60 |
| Gutta soh | 8.5 |
| Lecithin | 2 |
| Base III |  |
| Partially oxidized chicle | 98 |
| Lecithin | 2 |
| Base IV |  |
| Jelutong (dry) | 80 |
| Gutta siak | 18 |
| Lecithin | 2 |

The chewing gum may also include flavoring, such as sour or fruit flavoring or non-acid or mint flavoring in an amount ranging from about 0.3 to about 2.0% by weight, and preferably from about 0.5 to about 1.2% by weight of the final gum product. The flavoring may comprise synthetic flavors and oils derived from plants, leaves, flowers, fruit, etc. Representative flavor oils of this type include acids such as adipic, succinic and fumaric acid, citrus oils such as lemon oil, orange oil, lime oil, grapefruit oil, fruit essences such as apple essence, pear essence, peach essence, strawberry essence, apricot essence, raspberry essence, cherry essence, plum essence, pineapple essence, as well as the following essential oils: peppermint oil, spearmint oil, mixtures of peppermint oil and spearmint oil, clove oil, bay oil, anise oil, eucalyptus oil, thyme oil, cedar leaf oil, cinnamon oil, oil of nutmeg, oil of sage, oil of bitter almonds, cassia oil, and methylsalicylate (oil of wintergreen). Various synthetic flavors, such as mixed fruit, may also be incorporated in the chewing gum with or without conventional preservatives.

Where liquid flavors are employed, they may be added to the gum base-syrup mix as in the case of the particulate saccharin compound, that is, during the first five minutes of mixing, before a continuous mass of the gum base has been formed. Furthermore, after sugar (where present) has been mixed with the gum base, any of the above flavors, in the form of spray dried flavor with or without citric acid may be added.

In order to provide an initial taste or sensation of sourness, the chewing gum may also preferably contain an easily extractable food acid, for example, a water-soluble food acid, such as citric acid, tartaric acid or malic acid, in an amount ranging from about 0.3 to about 2.0% by weight, and preferably from about 0.5 to about 1.2% by weight of the final gum product. The chewing gum may also include, in addition to or in lieu of the easily extractable food acid, a poorly water-soluble food acid such as fumaric acid, succinic acid, or adipic acid in amounts ranging from about 0.5 to about 3.5% by weight of the chewing gum. The poorly water-soluble food acid will have a particle size of less than about 150 microns and will be retained in the gum base in a manner similar to the saccharin and fluoride compounds.

Regardless of the form of the saccharin and fluoride containing composition, whether it be a chewing gum or otherwise, as will be seen herein, the saccharin/fluoride combination may be employed with a fermentable carbohydrate such as sucrose or glucose or a non-cariogenic substitute such as sorbitol, xylitol, mannitol or the like. Inasmuch as the sugar, by itself, contributes to formation of dental plaque, the combination of a saccharin compound and a fluoride compound may be said to function as plaque-inhibiting agent to sugar. Sweeteners may be present in an amount ranging from about 90 to about 0.05%, preferably from about 90 to about 40%, and more preferably from about 85 to about 70% by weight of the final product. Examples of suitable sweeteners include but are not limited to:

A. Monosaccharides of 5 or 6 carbon atoms- arabinose, xylose, ribose, glucose, mannose, galactose, fructose, dextrose, or sorbose or mixtures of two ore more of the foregoing monosaccharides.
B. Disaccharides—sucrose such as cane or beet sugar, lactose, maltose or cellobiose; and
C. Polysaccharides—partially hydrolyzed starch, dextrin or corn syrup solids.
D. Polyhydric alcohols: sorbitol, xylitol, maltitol, and the like.

Generally, in forming the saccharin and aforementioned bulk sweetener containing composition, the saccharin compounds will be employed in a weight ratio to the natural sugar (water-soluble) sweetener within the range of from about 0.00022:1 to about 20:1 and preferably within the range of from about 0.0011:1 to about 0.01:1.

Of course, the saccharin, and fluoride compounds need not be employed with the sweetener; saccharides consumed separately from the saccharin compound or even sugar produced by breakdown of starches from previous meals may contribute to growth of S. mutans. In any event, the saccharin compound will act synergistically with the fluoride compound to inhibit growth of the S. mutans regardless of whether the saccharin is employed with cariogenic or non-cariogenic sweeteners.

The saccharin-fluoride combination of this invention may be provided in a variety of carriers in addition to chewing gum. For example, it may be utilized in formulating, for example, beverages, such as diet soda and hot and cold drinks sweetened with intense natural and/or artificial sweeteners.

Similarly, the compositions of this invention may utilize a beverage as a carrier for placing the syngeristic combination in the oral cavity. Since saccharin is employed as a sugar substitute in many beverages including diet carbonated beverages, low caloric soft drinks, such as iced tea and lemonade preparations, and hot beverages, such as hot chocolate, the subject combination of saccharin and fluoride may be readily incorporated into any of these well known and commercially available beverages.

The following example illustrates the synergistic effects when a saccharin and a fluoride are employed in combination to inhibit the growth of S. mutans.

EXAMPLE 1

A series of in vitro tests were performed to assess the effect of combinations of sodium fluoride and sodium saccharin on the growth of oral streptococci.

The materials employed and the methods followed are described below.

Microorganisms

Streptococcus mutans NCTC 10449 and Streptococcus mutans 6715-13 were used in these studies. Both strains were maintained either in a frozen ($-70°$ C.) or lyophilized state and were checked for authenticity prior to their commitment to these studies. For experimental use working cultures were maintained by twice monthly passage in fluid thioglycollate medium which contained 20% (vol/vol) meat extract and excess calcium carbonate.

Culture Conditions

The microorganisms were grown in defined chemical medium et al., Infec. Immun. 11:649, 1975] supplemented with either glucose or sucrose at a final concentration of 0.4% (wt/vol). The basal medium was sterilized using a membrane (0.45 um pore size) filtration technique. Sodium saccharin and sodium fluoride alone or in combination were added aseptically. The concentrations used in these studies are shown in Table 1 below.

Prior to use in the growth studies, the microorganism was adapted to the carbohydrate-supplemented basal medium by successively transferring cultures at least twice. From the final culture, which was in late logarithmic growth phase, 0.1 ml aliquots were used to inoculate the requisite growth media. All cultures were incubated at 37° C. under anaerobic conditions. Periodically, cultures were vigorously agitated on a vortex stirrer and the absorbance of the culture determined at an $O.D._{600\ nm}$ using a Spectronic 20 spectrophotometer.

TABLE 1

Scheme and Concentration of Sodium Fluoride and Sodium Saccharin Used in the Growth Studies

| Fluoride (ppm) (Present in the form of Sodium Fluoride) | Sodium Saccharin (%) | Fluoride (ppm) (Present in the form of Sodium Fluoride) | Sodium Saccharin (%) |
|---|---|---|---|
| 0.2 | 0.01 | 0.2 | 0.01 |
| 1.0 | 0.05 | 0.2 | 0.05 |
| 2.0 | 0.10 | 0.2 | 0.10 |
| 4.0 | 0.50 | 0.2 | 0.20 |
| 10.00 | 1.00 | — | — |
| 20.00 | 2.00 | 1.0 | 0.01 |
| 100.00 | — | 1.0 | 0.01 |
|  |  | 1.0 | 0.10 |
|  |  | 1.0 | 0.20 |
|  |  | 2.0 | 0.01 |
|  |  | 2.0 | 0.05 |
|  |  | 2.0 | 0.10 |
|  |  | 2.0 | 0.20 |
|  |  | 4.0 | 0.01 |
|  |  | 4.0 | 0.05 |
|  |  | 4.0 | 0.10 |
|  |  | 4.0 | 0.20 |
|  |  | 10.0 | 0.01 |
|  |  | 10.0 | 0.05 |
|  |  | 10.0 | 0.10 |
|  |  | 10.0 | 0.20 |

The results of these tests are shown in FIGS. 1A & B and 2A through E. A guide to the legends used in these figures is presented in Table 2 below.

TABLE 2

Legends to Figures

FIG. 1A: Growth kinetics of *S. mutans* strain NCTC 10449 in chemically defined medium supplemented with 0.4% glucose and either no saccharin (▲), 0.2% sodium saccharin (Δ), 0.5% sodium saccharin (●), or 1.0% sodium saccharin (o).

FIG. 1B: Growth kinetics of *S. mutans* strain NCTC 10449 in chemically defined medium supplemented with 0.4% glucose and either no sodium fluoride (▲), sodium fluoride in sufficient amounts to provide 4.0 ppm (Δ), 10.0 ppm fluoride (□), 20.0 ppm fluoride (⊕) or 100.00 ppm fluoride (o).

FIG. 2: Growth kinetics of *S. mutans* strain NCTC 10449 in chemically defined medium supplemented with 0.4% glucose and various levels of NaF and sodium saccharin, as follows:
  A. Fluoride at 0.2 ppm, all incubations, and sodium saccharin at 0.0% (o), 0.05% (▲), 0.10% (Δ), or 0.20% (●);
  B. Fluoride at 1.0 ppm, all incubations, and sodium saccharin at 0.0% (o), 0.05% (▲), 0.10% (Δ), or 0.20% (⊕);
  C. Fluoride at 2.0 ppm, all incubations, and sodium saccharin at 0.0% (o), 0.05% (▲), 0.10% (Δ), or 0.20% (●);
  D. Fluoride at 4.0 ppm, all incubations, and sodium saccharin at 0.0% (o), 0.05% (▲), 1.10% (Δ), or 0.20% (●);
  E. Fluoride at 10.0 ppm, all incubations, and sodium saccharin at 0.0% (o), 0.01% (▲), 0.05% (Δ), 0.10% (□), or 0.20% (●).

FIG. 3A: Growth kinetics of *S. mutans* strain 6715-13 in chemically defined medium supplemented with 0.4% sucrose and either no saccharin (▲), 0.2% sodium saccharin (Δ), 0.5% sodium saccharin (●), or 1.0% sodium saccharin (o).

FIG. 3B: Growth kinetics of *S. mutans* 6715-13 in chemically defined meduim supplemented with 0.4% sucrose and either no sodium fluoride (▲), or sodium fluoride in sufficient amount to provide 4.0 ppm fluoride (Δ), 10.0 ppm fluoride (●), 20.0 ppm fluoride (o), or 100.0 ppm fluoride (□).

FIG. 4: Growth kinetics of *S. mutans* strain 6715-13 in chemically defined medium supplemented with 0.4% sucrose and various levels of NaF and sodium saccharin, as follows:
  A. Fluoride at 0.2 ppm, all incubations, and sodium saccharin at 0.0% (o), 0.05% (▲), 0.10% (Δ), or 0.20% (●);
  B. Fluoride at 1.0 ppm, all incubations, and sodium saccharin at 0.0%, (o), 0.05% (▲), 0.10% (Δ), or 0.20% (●);
  C. Fluoride at 2.0 ppm, all incubations, and sodium saccharin at 0.0% (o), 0.5% (▲), 0.10% (Δ), or 0.20% (●);
  D. Fluoride at 4.0 ppm, all incubations, and sodium saccharin at 0.0% (o), 0.01% (▲), 0.05% (Δ), or 0.10% (●).
  E. Fluroide at 10.0 ppm, all incubations, and sodium saccharin at 0.0% (o), 0.01% (▲), 0.05% (Δ), or 0.10% (●).

From these studies it is apparent that the addition of sodium saccharin to either glucose-or sucrose-grown cultures affected the growth pattern of both strains *S. mutans*. The pattern of inhibition was shown to be concentration dependent, with concentrations greater than 0.2% being inhibitory (FIG. 1A). Similarly, the addition of sodium fluoride to either glucose-or sucrose-grown cultures affected the growth rate of *S. mutans*. The pattern of inhibition was again concentration-dependent with 10.0 ppm fluoride being the lowest concentration noticeably affecting the growth rate (FIG. 1B).

The addition of both sodium fluoride and sodium saccharin to the respective cultures indicated the pattern of inhibition could be demonstrated at levels below those required when the compounds were used alone. FIG. 2A and 2B illustrate that sodium saccharin, at levels greater than 0.1% in the presence of 0.2 ppm or 1.0 ppm fluoride decreased the final growth yield and that all concentrations of sodium saccharin tested delayed the initiation of logarithmic growth. In the presence of fluoride at a concentration of 2.0 ppm (FIGS. 2C and 4C), it was shown that the inclusion of sodium saccharin even at a level of 0.05% increased the growth lag, i.e., that time before the cocci started to divide. The addition of 0.1% and 0.2% sodium saccharin to the defined growth medium containing 2.0 ppm fluoride noticeably decreased the final growth yields of these cultures. The lag time was also progressively increased when fluoride was increased to 4.0 ppm (FIGS. 2D and 4D).

FIGS. 2E and 4E illustrate the effect of various concentrations of sodium saccharin in the presence of 10.0 ppm fluoride on the growth pattern of glucose-adapted *S. mutans* NCTC 10449 and sucrose-adapted *S. mutans*

6715-13, respectively. The addition of sodium saccharin, as little as 0.01%, significantly increased the time required for the culture to initiate logarithmic growth. At concentrations as low as 0.05% of sodium saccharin both the growth rate and final growth yields of *S. mutans* were noticeably diminished.

Thus, sodium saccharin at a concentration of 0.2% affects the growth pattern of *S. mutans* NCTC 10449 and *S. mutans* 6715-13 adapted to growth in glucose and sucrose-supplemented defined growth media. Similarly, fluoride at a concentration of 10.0 ppm also perturbs the growth pattern of these strains. When these two compounds are incorporated into the growth medium together, the concentrations required to perturb the growth pattern is greatly reduced. Thus, these two agents appear to have a synergistic action on the growth pattern of *S. mutans* NCTC 10449. Growth inhibition is reflected by three parameters, increased lag (most sensitive), decreased growth yields, and decreased growth rate (least sensitive). The synergistic combination of this invention is effective in inhibiting the growth of *S. mutans* at a saccharin concentration of at least 0.05%, calculated as the sodium salt, and a minimum fluoride concentration of at least 0.2 ppm in the form of the sodium salt, said concentrations being the concentrations of these materials in the salivary fluids bathing *S. mutans* colonies with the dental plaque.

The following Examples further illustrate the present invention without, however, limiting the same thereto. All temperatures are expressed in °F.

EXAMPLE 2

A cherry flavor saccharin-sugar containing chewing gum is prepared from the following ingredients:

|  | Parts by Weight |
|---|---|
| Gum Base | 20 |
| Sugar | 50 |
| Corn Syrup | 16 |
| Dextrose | 10 |
| Lecithin | 0.2 |
| Citric acid | 0.5 |
| Fumaric acid (passes through a U.S. 140 mesh screen) | 2 |
| Free saccharin acid (passes through a U.S. 140 mesh screen) | 0.1 |
| Calcium fluoride (passes through a U.S. 140 mesh screen) | 0.2 |
| Artificial cherry flavor | 1 |
| Gum arabic coated cherry flavor | 1.5 |

The gum base is melted (temperature 270°) and placed in a standard dough mixer kettle equipped with sigma blades. The corn syrup and lecithin are added and mixed for 2 minutes at 200°. At the time the mix is folding well, powdered free saccharin, powdered fluoride and powdered fumaric acid are added to the base-syrup mix and the mixture is mixed for 1 minute at 200°. Thereafter, the sucrose, dextrose, flavor oil, citric acid, and coloring agents are added and blended with the above mixture for 5 minutes at 160°. The resulting gum is discharged from the kettle and formed into gum sticks employing conventional techniques.

The chewing gum product obtained is found to have a pleasant balanced sweet-sour taste for up to 30 minutes and is effective in inhibiting growth of *S. mutans* in the oral cavity.

EXAMPLE 3

A peppermint flavor saccharin-sugar containing chewing gum is prepared from the following ingredients:

|  | Parts by Weight |
|---|---|
| Gum base | 20 |
| Corn Syrup, 44° Be' | 17 |
| Powdered free saccharin acid (pulverized to pass through a U.S. 140 mesh screen) | 0.1 |
| Powdered Sodium fluoride (pulverized to pass through a U.S. 140 mesh screen) | 0.2 |
| Powdered Sugar (sucrose) | 50 |
| Dextrose | 10 |
| Peppermint oil | 1 |
| Lecithin | 0.2 |

The gum base is melted (temperature 270°) and placed in a standard dough mixer kettle equipped with sigma blades. The corn syrup and lecithin are added and mixed for 2 minutes at 200°. At the time the mix is folding well, powdered free saccharin and powdered fluoride are added and the mixture is mixed another 3 minutes at 200°. Thereafter, the sucrose, dextrose and flavor oil are added during which time the mixture is mixed another 3 minutes at 200°. Thereafter, the sucrose, dextrose and flavor oil are added during which time the mixture is mixed another 5 minutes. The gum is then discharged from the kettle, cut into 25 lb. loaves and allowed to cool to 90°-120° F. It is then rolled to a thickness of 0.178 cm of a standard Gimpel machine and scored into strips 7.26 cm wide and 41.9 cm long, and cooled for 12-18 hours.

The chewing gum product obtained is found to have a pleasant sweet taste for up to 30 minutes and inhibits growth of *S. mutans* in the oral cavity.

EXAMPLE 4

A spearmint flavor saccharin-sugar containing chewing gum is prepared from the following ingredients:

|  | Parts by Weight |
|---|---|
| Gum Base | 20 |
| Sugar (sucrose) | 52 |
| Corn Syrup 44 Be' | 17 |
| Dextrose | 10 |
| Lecithin | 0.2 |
| Free saccharin (powdered - passes through a 140 U.S. mesh screen) | 0.1 |
| Calcium fluoride (powdered - passes through a 140 U.S. mesh screen) | 0.2 |
| Spearmint oil | 0.6 |

The gum base is melted (temperature 270°) and placed in a standard dough mixer kettle equipped with sigma blades. The corn syrup and lecithin are added and mixed for 2 minutes at 200°. At the time the mix is folding well, powdered free saccharin, powdered fluoride and flavor oil are mixed for 1 minute at 200°. Thereafter, the sucrose dextrose and coloring agents are added and blended with the above mixture for 5 minutes at 160°. The resulting gum is discharged from the kettle and formed into gum sticks as described in Example 1.

The chewing gum product obtained is found to have a pleasant sweet taste for up to 30 minutes and inhibits growth of *S. mutans* in the oral cavity.

EXAMPLE 5

A spearmint flavored saccharin/calcium fluoride sugar-containing chewing gum is prepared from the following ingredients:

|  | Parts by Weight |
| --- | --- |
| Gum Base | 18.5 |
| Sodium saccharin | 0.2 |
| Calcium fluoride | 0.2 |
| Chalk | 3.3 |
| Sugar | 49 |
| Corn syrup | 17 |
| Lecithin | 0.2 |
| Sorbitol | 10 |
| Spearmint flavor (oil) | 1 |
| Spearmint (Spray-dried) | 0.5 |

The gum base is melted at 140°-150° F. and chalk premixed with sodium saccharin and calcium fluoride (particle size-64 microns and less) is added and the mixture mixed in a standard dough mixer equipped with sigma blades. Sugar is added and mixed for 3 minutes at 200°. Thereafter, liquid flavor is added and mixed for 2 minutes, a premix of lecithin and corn syrup is added and mixed for 3 minutes, sorbitol is added and mixed for 1 minute and spray dried flavor is added and mixed for 1 minute. The resulting gum is discharged from the kettle and formed into gum sticks employing conventional techniques.

The chewing gum product obtained is found to have a pleasant balanced sweet taste for up to 30 minutes and is effective in inhibiting growth of *S. mutans* in the oral cavity.

We claim:

1. In the method of inhibiting the growth of *Streptococcus mutans* by contacting *Steptococcus mutans* with a saccharin compound selected from the group consisting of sodium saccharin, ammonium saccharin, calcium saccharin, or the free acid form of saccharin in an amount sufficient to inhibit growth of *Streptococcus mutans*, the improvement comprising contacting *Streptococcus mutans* with said saccharin in synergistic combination with a fluoride material in an amount which inhibits or prevents growth of *Streptoccus mutans*.

2. The method of claim 1 wherein said saccharin is contacted with *Streptococcus mutans* in a composition having no more than 1.0% saccharin and said fluoride material is present in said composition in an amount of no more than 100 ppm of fluoride.

3. The method of claim 2 wherein said saccharin is present in said composition in an amount of no more than about 0.2% saccharin and said fluoride material present in said composition in an amount of no more than about 10 ppm of fluoride.

4. The method of claim 3 wherein said saccharin is present in said composition in an amount of no more than about 0.05% saccharin and said fluoride material is present in said composition in an amount of at least 0.2 ppm fluoride.

5. The method of claim 1 wherein said synergistic combination is contacted with *Streptococcus mutans* for a period of about 30 minutes.

* * * * *